(12) United States Patent
McKeown

(10) Patent No.: US 12,208,214 B2
(45) Date of Patent: Jan. 28, 2025

(54) SYSTEMS, DEVICES AND METHODS FOR SLEEP THERAPY USING VESTIBULAR NERVE STIMULATION

(71) Applicant: Neurovalens Ltd., Portglenone (GB)

(72) Inventor: Jason McKeown, Portglenone (GB)

(73) Assignee: Neurovalens Limited, Portglenone (GB)

(*) Notice: Subject to any disclaimer, the term of this patent is extended or adjusted under 35 U.S.C. 154(b) by 516 days.

(21) Appl. No.: 16/866,478

(22) Filed: May 4, 2020

(65) Prior Publication Data

US 2020/0360653 A1 Nov. 19, 2020

Related U.S. Application Data

(60) Provisional application No. 62/843,310, filed on May 3, 2019.

(51) Int. Cl.
*A61M 21/02* (2006.01)
*A61N 1/04* (2006.01)
(Continued)

(52) U.S. Cl.
CPC ........... *A61M 21/02* (2013.01); *A61N 1/0456* (2013.01); *A61N 1/0526* (2013.01);
(Continued)

(58) Field of Classification Search
CPC . A61M 21/02; A61M 2210/06; A61N 1/0456; A61N 1/0526
(Continued)

(56) References Cited

U.S. PATENT DOCUMENTS 6,314,324 B1 * 11/2001 Lattner ................. A61N 1/3601
600/26
7,856,275 B1 * 12/2010 Paul .................... A61N 1/36014
607/55
(Continued)

FOREIGN PATENT DOCUMENTS

JP 5327542 B2 * 10/2013 ............ A61M 21/02

OTHER PUBLICATIONS

Krystal et al. ("The Effect of Vestibular Stimulation in a Four-Hour Sleep Phase Advance Model of Transient Insomnia" J Clin Sleep Med. Aug. 15, 2010;6(4):315-21. PMID: 20726278; PMCID: PMC2919660) (Year: 2010).*

(Continued)

*Primary Examiner* — Christine H Matthews
*Assistant Examiner* — Marc D. Honrath
(74) *Attorney, Agent, or Firm* — Eleanor Musick; Torrey Pines Law Group PC

(57) ABSTRACT

Methods, systems and devices are provided to stimulate the vestibular system in such a way as to excite the neurological components of the circadian rhythm system and induce sleep. A device with one or more electrodes placed over a subject's scalp provides vestibular nerve stimulation (VeNS) to the vestibular nerve, which is then carried into the vestibular nucleus in the brainstem and thereafter transmitted to the neurological components of the circadian rhythm system to excite the areas that promote sleep, allowing the body to enter the sleep state. The characteristics of the stimulation signal and duration of the treatment are configured to allow the treatment to be delivered in advance of the subject's desired sleep time so that the device does not need to be worn in bed.

16 Claims, 14 Drawing Sheets

(51) Int. Cl.
*A61N 1/05* (2006.01)
*A61N 1/36* (2006.01)
*A61M 21/00* (2006.01)

(52) U.S. Cl.
CPC . *A61N 1/36034* (2017.08); *A61M 2021/0072* (2013.01); *A61M 2210/06* (2013.01)

(58) Field of Classification Search
USPC .......................................................... 600/26
See application file for complete search history.

(56) References Cited

U.S. PATENT DOCUMENTS

| | | | | |
|---|---|---|---|---|
| 2002/0072781 | A1* | 6/2002 | Lattner | A61N 1/36036 607/42 |
| 2004/0215236 | A1* | 10/2004 | Lattner | A61N 1/36036 607/2 |
| 2009/0082831 | A1* | 3/2009 | Lattner | A61N 1/36031 607/59 |
| 2012/0203309 | A1* | 8/2012 | Englehart | A61M 21/02 607/2 |
| 2013/0090704 | A1* | 4/2013 | Kolen | A61N 1/0476 607/45 |
| 2013/0303953 | A1* | 11/2013 | Lattner | A61H 23/0245 601/47 |
| 2017/0182285 | A1* | 6/2017 | Tyler | A61B 5/4806 |
| 2017/0304616 | A1* | 10/2017 | McGeoch | A61N 1/0456 |
| 2018/0193641 | A1* | 7/2018 | Black | A61M 21/02 |

OTHER PUBLICATIONS

Krystal, A. D., Zammit, G. K., & Wyatt, J. K. (2010). The effect of vestibular stimulation in a four-hour sleep phase advance model of transient insomnia. Journal of Clinical Sleep Medicine, 06(04), 315-321. https://doi.org/10.5664/jcsm.27871 (Year: 2010).*

Bayer, L., Constantinescu, I., & Perrig, S. (2011). Rocking synchronizes brain waves during a short nap. Current Biology, 21(12). https://doi.org/10.1016/j.cub.2011.05.012 (Year: 2011).*

Yamamoto Y, Struzik ZR, Soma R, Ohashi K, Kwak S. Noisy vestibular stimulation improves autonomic and motor responsiveness in central neurodegenerative disorders. Annals of neurology. 2005;58(2):175-81. Epub Jul. 29, 2005. doi: 10.1002/ana.20574. PubMed PMID: 16049932. (Year: 2005).*

* cited by examiner

SYSTEMS, DEVICES AND METHODS FOR SLEEP THERAPY USING VESTIBULAR NERVE STIMULATION

RELATED APPLICATIONS

This application claims the priority of U.S. Provisional Application No. 62/843,310, filed May 3, 2019, which is incorporated herein by reference in its entirety.

BACKGROUND

Field of the Invention

Systems, methods and devices provided herein relate to vestibular stimulation, and more specifically to stimulating the vestibular nucleus to promote sleep.

Related Art

Sleep is becoming a more prominent topic in human health due to increasing links between poor sleep and poor health. While some sleep disorders such as insomnia or sleep apnea are widely known and have a variety of accepted treatments, much is still not known about how the body generally regulates sleep or the external and internal factors that influence the body's ability to sleep. As the links between sleep and overall health increase, there has been a greater focus on understanding how the body, and specifically the brain, regulates sleep.

There are many areas within the brain stem that control automatic functions of the body, such as blood pressure, heart rate, kidney function, body fat and sleep. As with many brain functions, sleep is a complex process that is influenced by different physiological and neurological factors. Key areas of the brain thought to influence sleep include the hypothalamus, the suprachiasmatic nucleus (SCN) and the intergeniculate leaflet (IGL). These are thought to act as the circadian rhythm clock that tells the body when it's time to sleep and when it's time to wake up. Thus, attempts to regulate the circadian rhythm through these key anatomical brain features may lead to ways to promote sleep.

The vestibular system may be one pathway to regulating the circadian rhythm and influencing sleep. The vestibular system is a major contributor to our sense of balance and spatial orientation, and consists in each inner ear of three semicircular canals (which detect rotational movement) and the two otolith organs, termed the utricle and saccule, which detect linear acceleration and gravity (Khan & Chang, 2013). They are called otolith organs as they are fluid filled sacs containing numerous free moving calcium carbonate crystals—called otoliths—which move under the influence of gravity or linear acceleration to act upon receptor cells to alter vestibular afferent nerve activity.

One pathway to regulating sleep via the circadian rhythm system may be through the vestibular system, as the circadian rhythm system has been found to receive input from the vestibular nuclei. The vestibular nuclei (in particular, the medial vestibular nucleus or "MVe") are located in the pons and medulla and receive input via the vestibular nerve from the vestibular system. The MVe are thought to project (both directly and indirectly via the parieto-insular vestibular cortex (PIVC)) to the brainstem homeostatic sites of the parabrachial nucleus (PB) and the peri-aqueductal gray (PAG) (see Chapter 1 and Chapter 3, Section 8 in doctoral thesis by McGeoch, 2010). The PB seems to act to maintain homeostasis—i.e., a stable internal physiological milieu— by integrating this vestibular input with sympathetic input (via lamina 1 spino- and trigemino-thalamic tract fibers) and parasympathetic input (via the nucleus of the solitary tract) (Balaban and Yates, 2004; Craig, 2007; Craig, 2009; McGeoch et al., 2008, 2009; McGeoch, 2010).

It is thought that the PB then acts to maintain homeostasis by means of behavioral, neuroendocrine, and autonomic nervous system efferent (i.e., both sympathetic and parasympathetic) responses (Balaban and Yates, 2004; McGeoch, 2010). Anatomically the PB projects to the insula and anterior cingulate, amygdala and hypothalamus. The insula and anterior cingulate are areas of cerebral cortex implicated in emotional affect and motivation, and hence behavior (Craig, 2009). The hypothalamus plays a vital role in coordinating the neuroendocrine system (Balaban and Yates, 2004; Fuller et al., 2004; Craig, 2007). The amygdala (together again with the hypothalamus and insula) is similarly known to be important in autonomic nervous system control. The PB also outputs to the PAG and basal forebrain, which are also involved in homeostasis (Balaban and Yates, 2004).

Vestibular nerve stimulation ("VeNS") activates all five components of the vestibular apparatus simultaneously using an electrical current (Fitzpatrick & Day, 2004; St. George & Fitzpatrick, 2011), and offers the practical option of being produced commercially for home use without expert supervision. VeNS involves stimulating the vestibular system through the transcutaneous application of a small electric current (usually between 0.1 to 3 milliamps (mA)) via two electrodes. The electrodes can be applied to a variety of locations around the head, but typically one is applied to the skin over each mastoid process, i.e., behind each ear. Some authors term this a "binaural application." If a cathode and an anode are used with one placed over each mastoid, which is the most common iteration, then this is termed a bipolar binaural application of VeNS. The current can be delivered in a variety of ways, including a constant state, in square waves, a sinusoidal (alternating current) pattern and as a pulse train (Petersen et al., 1994; Carter & Ray, 2007; Fitzpatrick & Day, 2004; St. George & Fitzpatrick, 2011).

There have been limited efforts to affect sleep using vestibular stimulation. One effort is described in U.S. Pat. No. 6,314,324 to Lattner et al. and relies upon known vestibular treatments of counteracting vertigo by rhythmically stimulating the semicircular canal, saccule, utrical and/or ampullae. The stimulation created an artificial rocking sensation that mimics the feeling of being physically rocked back and forth, as with a baby in a bassinet. However, this therapy is designed to be carried out while a person is lying in bed so the rocking sensation will gently induce sleep and is designed to be worn during sleep to provide additional stimulation if the user's sleep pattern is disrupted.

Therefore, there is a need for further development of methods and devices to more effectively and efficiently provide vestibular stimulation to promote sleep.

SUMMARY

Embodiments described herein provide for systems, devices and methods for utilizing vestibular stimulation to promote sleep by influencing key areas of the brain responsible for regulating the circadian rhythm to excite areas that promote sleep and decrease wakefulness. Stimulation can be delivered for a period of time prior to going to bed using customized signal shapes and durations delivered to the vestibular nerves via a head-mounted portable electronic device that does not require that the user be in bed, as it avoids creating a rocking sensation that might affect a user's balance. The stimulation essentially tells the brain that it's time to go to sleep, providing an effective method for promoting sleep without requiring a user to wear a device to bed or be in bed for it to be effective.

In one embodiment, a method of promoting sleep in a human subject through delivery of vestibular nerve stimulation (VeNS) comprises: positioning at least one electrode into electrical contact with the human subject and proximate to a location of the subject's vestibular system; and delivering VeNS to the human subject from a current source connected with the at least one electrode, wherein the VeNS is delivered prior to the subject's desired sleep time.

In another embodiment, a method of treating insomnia with vestibular nerve stimulation, comprises: positioning at least one electrode into electrical contact with the human subject and proximate to a location of the subject's vestibular system; and delivering VeNS to the human subject from a current source connected with the at least one electrode, wherein the VeNS is delivered prior to the subject's desired sleep time.

In a still further embodiment, a device for promoting sleep in a human subject, the device comprises: electrodes disposed in electrical contact with the subject's scalp at a location corresponding to the subject's vestibular system; and a current source in electrical communication with the electrodes for delivering vestibular nerve stimulation (VeNS) to the subject, wherein the current source delivers VeNS for approximately 30 to approximately 60 minutes and within approximately 1 to approximately hours of the subject's desired sleep time.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for stimulation of the vestibular system in such a way as to excite the neurological components of the circadian rhythm system and induce sleep. For example, one method disclosed herein allows for a device with one or more electrodes placed over a subject's scalp to deliver vestibular nerve stimulation (VeNS) to the vestibular nerve, which is then carried into the vestibular nucleus in the brainstem and thereafter transmitted to the neurological components of the circadian rhythm system to excite the areas that promote sleep, allowing the body to enter the sleep state. The characteristics of the stimulation signal and duration of the treatment are configured to allow the treatment to be delivered in advance of the subject's desired sleep time so that the device does not need to be worn in bed.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Pathways for Sleep Therapy

Figure 1:
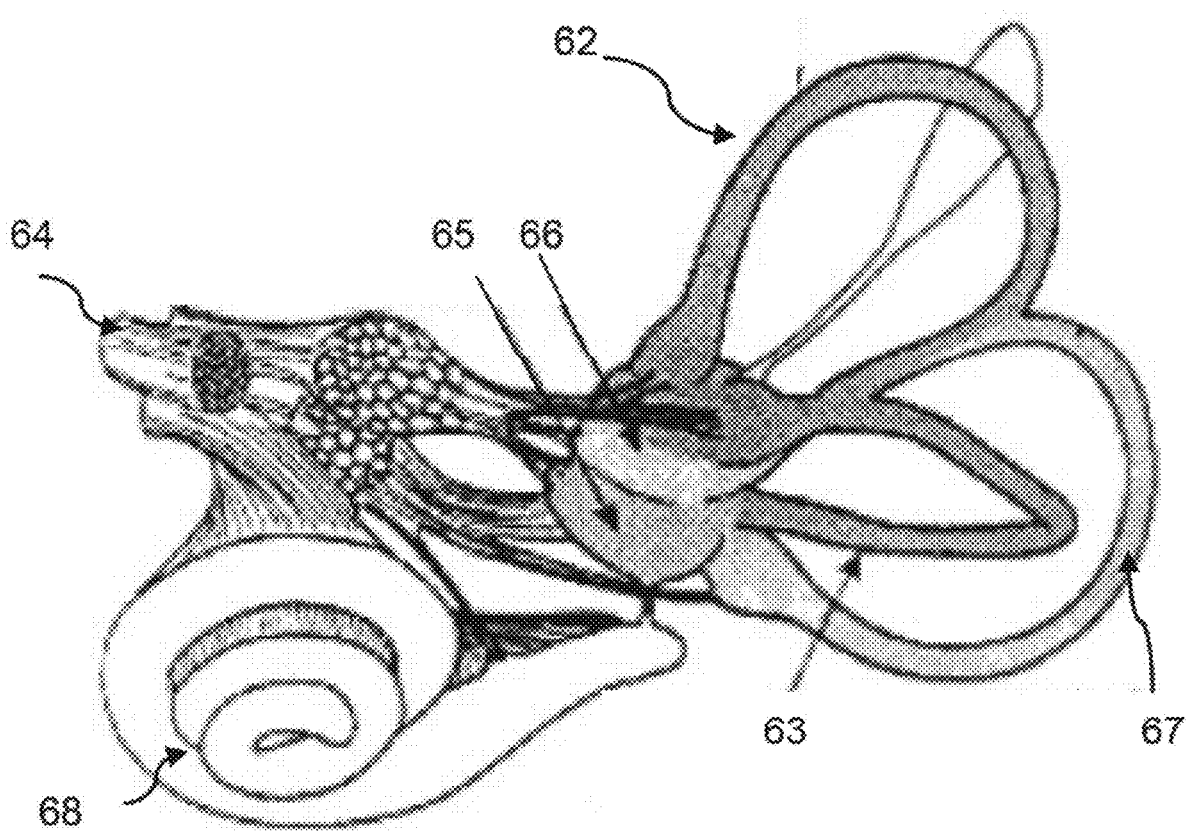
FIG. 1 is a diagram illustrating the vestibular system of the left inner ear.

FIG. 1 illustrates the vestibular system of the left inner ear. The cochlea 68, which is the peripheral organ of hearing, is also shown. It demonstrates: the anterior 62, posterior 67, and horizontal 63 semicircular canals, which transduce rotational movements; and the otolith organs (the utricle 66 and saccule 65), which transduce linear acceleration and gravity. The vestibulocochlear nerve 64 (also known as the eighth cranial nerve) is composed of the cochlear nerve (which carries signals from the cochlea), and the vestibular nerve (which carries signals from the vestibular system).

Figure 2:
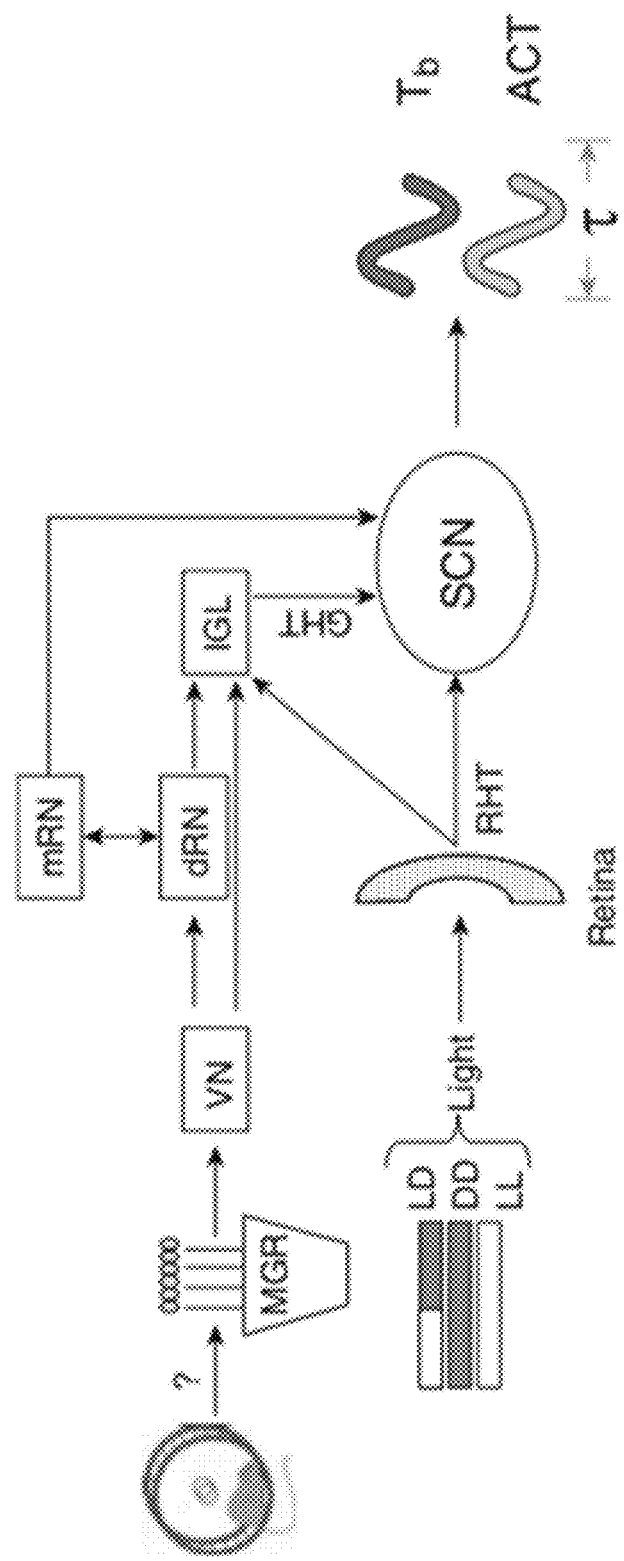
FIG. 2 is a model illustrating anatomical features linking the vestibular and circadian timing systems (CTS)

FIG. 2 is a model outlining potential anatomical features linking the vestibular and circadian timing systems (CTS). Light, the primary synchronizing agent for the CTS, is transmitted to the suprachiasmatic nucleus (SCN) via the retinohypothalamic tract (RHT). Nonphotic stimuli, such as locomotor activity (running wheel), are transmitted to the SCN via the intergeniculate leaflet (IGL) and the geniculohypothalamic tract (GHT). There is also evidence supporting involvement of the serotonergic midbrain raphe (dorsal and medial, dRN and mRN, respectively) in the transmission of activity information to the SCN and IGL. Morphological data also suggest that the vestibular nuclei (VN) may influence the raphe nuclei, particularly the dRN. MGR are the macular gravity receptors, T is the circadian period, and Tb is body temperature.

Vestibular stimulation activates key areas of the brain related to sleep indirectly by using the vestibular nucleus as a relay, transmitting stimulation of the vestibular system from the vestibular nucleus to the SCN, IGL and hypothalamus. These neurological components act as the circadian rhythm system and influence sleep in the human body, so the application of VeNS essentially re-regulates the circadian rhythm and excites the areas that promote sleep (while decreasing wakefulness), allowing the body to enter the sleep state at the correct time.

Treatment Methods

Figure 3:
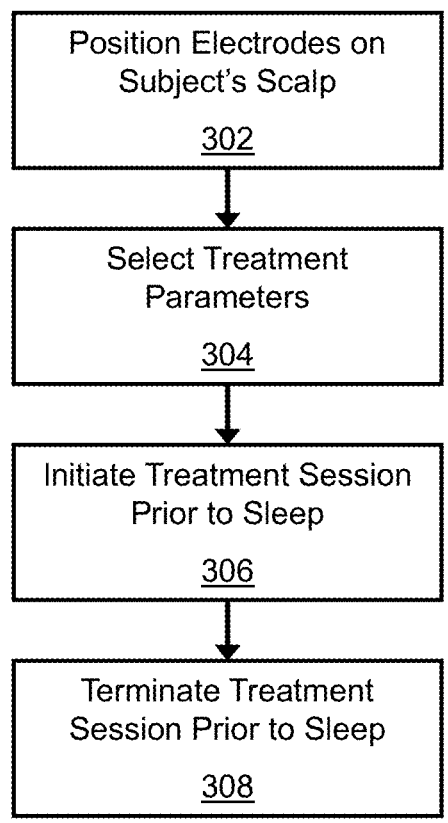
FIG. 3 is a flow diagram illustrating an example method for utilizing VeNS to affect sleep, according to an embodiment of the invention.

FIG. 3 illustrates one embodiment of a method of utilizing VeNS to affect sleep in a human subject. In step 302, one or more electrodes are positioned on the subject's scalp proximate to the location of the vestibular system. The electrodes may be placed on one or both sides of the scalp near the approximate location where stimulation of the vestibular nerve can be achieved. In step 304, the parameters of the VeNS treatment are configured on the VeNS device depending on one or more factors relating to the treatment or the subject, such as the signal shape, pulse, frequency, duration of treatment, desired sleep time relative to the treatment time, etc. Once the parameters are selected, the treatment session may be initiated in step 306 prior to the subject's desired sleep time. In step 308, at the end of the desired treatment duration, the treatment is terminated prior to the subject's sleep time.

Although not part of the primary method, the subject's response to the treatment may be monitored to determine the effectiveness of the treatment, for example via remote or wearable sensors, the subject's own observations about their sleep quality and duration, and other physiological and psychological factors that may be measured over longer periods of time after multiple treatment sessions. The subject's response to the treatment may be utilized to adjust the overall treatment schedule, the parameters of the VeNS or other observed factors that may be influencing the subject's sleep.

The method of treatment may include delivery of vestibular stimulation at a range of frequencies that are effective at re-regulating the circadian rhythm. In one embodiment illustrated in FIG. 4, the parameters of a VeNS treatment includes use of a square wave with a frequency of approximately 0.25 Hz and a current range of approximately 0.01 mA-1 mA delivered at an approximately 50 percent duty cycle. The electrodes may be placed bilaterally for delivery of stimulation to both sides of the user's head. The session length of treatment may be approximately 30 minutes to approximately 60 minutes, and the subject may initiate treatment within approximately 3 hours before the expected initiation of sleep.

In another embodiment, the method of treatment may include delivery of vestibular stimulation at varying parameters that may be effective for different types of subjects or with different outcomes relating to the timing of the treatment and the intended start of the sleep cycle. For example, a range of frequencies from approximately 0.0001 Hz to approximately 10000 Hz, with a range of approximately 0.01 mA to approximately 5 mA, may be utilized with any type of waveform and duty cycle, from square to sinusoidal to pulse. The treatment may be delivered via only one electrode placed on one side of the user's head at the approximate location where stimulation of the vestibular nerve can be made. The user may initiate a treatment at any time prior to going to bed and initiate a treatment session of anywhere from approximately 1 minute to approximately 120 minutes.

It is also notable that the stimulation is delivered in such a way as to promote sleep within the circadian rhythm section without creating a rocking sensation, through the delivery of stimulation at approximately 0.25 Hz and at least below approximately 0.5 Hz. These frequencies, which are sometimes referred to as "subsensory VeNS," are slow and provide low enough power to avoid creating the rocking sensation, allowing the subject to receive the VeNS prior to getting into bed and then terminating the treatment session prior to getting into bed. In contrast, a frequency of around 25 Hz has also proven effective and is by contrast too high for the subject to detect. The device can be removed after getting into bed, eliminating any potential discomfort that often results from other devices that are required to be worn in bed while trying to fall asleep.

Validation

A comparable commercially available VeNS device sold under the trademark VESTIBULATOR™ (Good Vibrations Engineering Ltd. of Ontario, Canada) has previously been used in a number of research studies at other institutions. (Barnett-Cowan & Harris, 2009; Trainor et al., 2009.) This device functions with 8 AA batteries, so that the voltage can never exceed 12 V. According to the manufacturer's specifications, the maximum current that this device can deliver is 2.5 mA. The present invention uses a more user-friendly device (e.g., the delivered current can be adjusted using a controller (knob, slide, or similar) on the side of the housing, in comparison to the VESTIBULATOR™, where a similar adjustment can only be carried out by first writing a MATLAB® script and then uploading it remotely, via BLUETOOTH®, in order to reprogram the VESTIBULATOR's™ settings.)

Due to the very small currents used during VeNS, the technique is believed to be safe (Fitzpatrick & Day, 2004; Hanson, 2009). In particular, although electrical current can lead to cardiac arrhythmias, including ventricular fibrillation, the threshold for such an occurrence is in the 75 to 400 mA range, well above the current levels the battery powered VeNS devices can deliver. Furthermore, the electrodes will only be applied to the scalp, such as shown in FIG. 14, and nowhere near the skin over the chest.

Resistive heating can occur with high voltage electrical stimulation of the skin. However, the voltage and current (usually below 1 mA) delivered during VeNS are well below the levels that pose this risk. Nonetheless, skin irritation can occur due to changes in pH. This may be mitigated by using large surface area (approximately 2 inch diameter) platinum electrodes and aloe vera conducting gels.

It may be desirable to monitor the subject's heart rate (HR) to determine the cardiac frequency during VeNS treatment. The cardiac frequency can then be used to alter the frequency of the sinusoidal VeNS so as to maintain a certain ratio between the cardiac frequency and the frequency of the sinusoidal VeNS to avoid interference with baroreceptor activity. For example, a sinusoidal VeNS frequency to cardiac frequency ratio of 0.5 would be appropriate.

Figure 14:
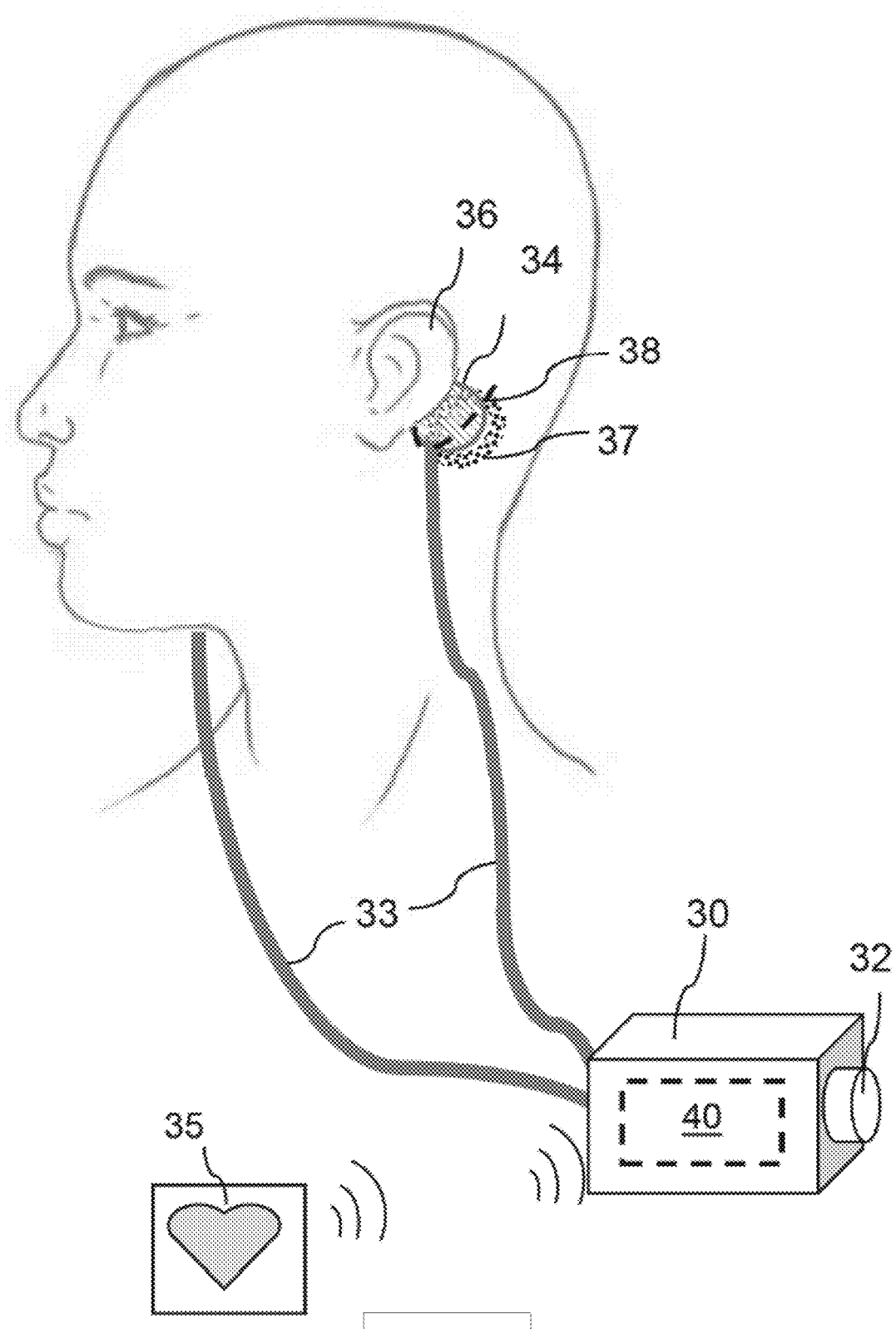
FIG. 14 is a diagram showing an exemplary VeNS electrode placement, according to one embodiment of the invention.

During administration of VeNS, one platinum electrode is attached to the skin over one mastoid and the other electrode attached to the skin over the other, as shown in FIG. 14. The electrodes may be coated with conducting gel containing aloe vera. The device is activated to deliver a current of approximately 0.1 mA (given a trans-mastoid resistance of about 500 kOhm) with a sinusoidal waveform at approximately 0.25 Hz. A typical current range for the device would be around 0.001 mA to around 5 mA. The subject should remain seated or lying flat throughout the session to avoid mishap due to altered balance during vestibular stimulation. The device is set up to automatically stop after one hour however, the subject may discontinue the treatment sooner if desired. The subject should remain seated until their balance has returned to normal, which should occur within a short period of time after the VeNS device has been turned off.

Figure 4:
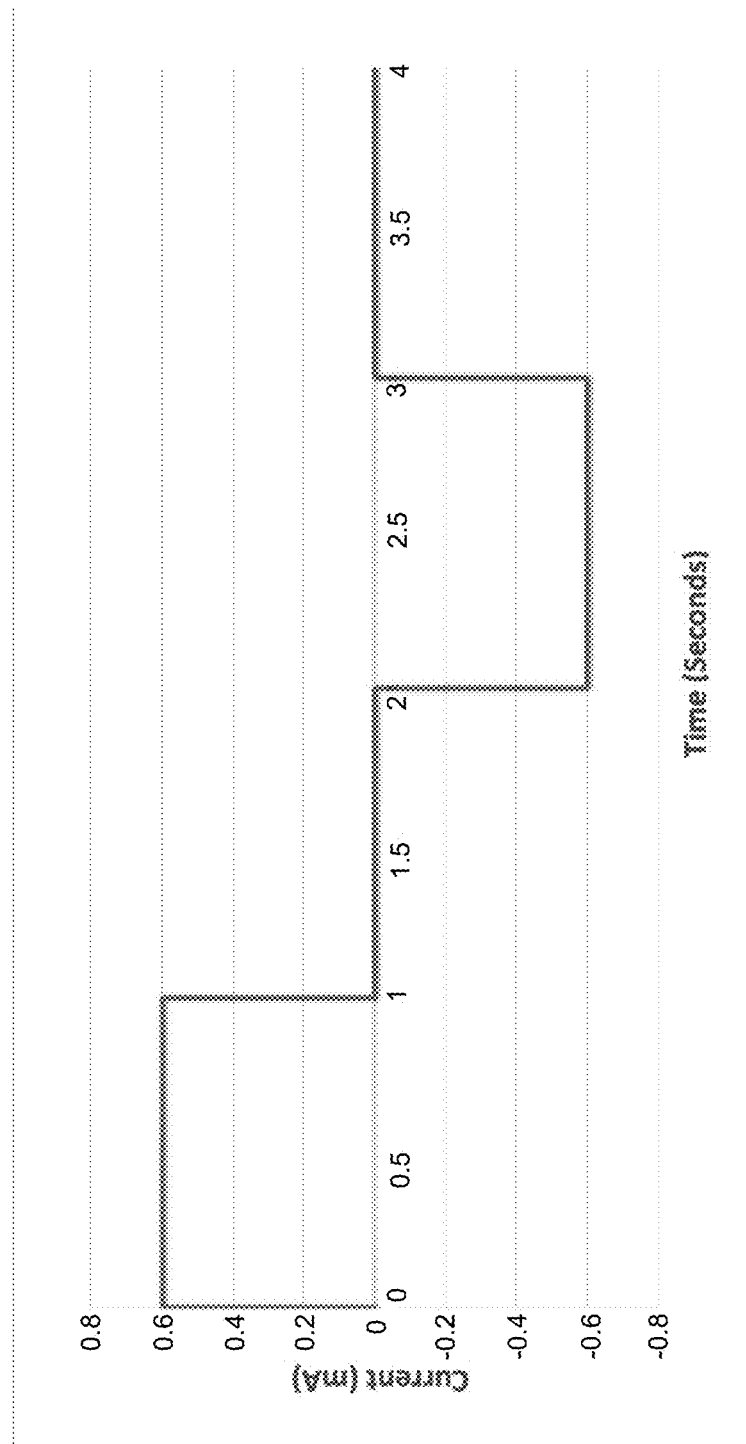
FIG. 4 is a diagram illustrating an exemplary wave form for use in delivering VeNS, according to one embodiment of the invention.

In one embodiment, a VeNS device provided by the company Neurovalens Ltd was used to deliver the stimulation. This device delivers a VeNS current waveform as illustrated in FIG. 4, which consists of an AC square wave at 0.25 Hz with a 50% duty cycle. The protocol followed was that for the first 30 minutes each subject underwent indirect calorimetry alone in order to establish a baseline. Each subject then underwent a one-hour session of binaural, bipolar VeNS with electrodes placed on the skin over each mastoid as shown in FIG. 14. As stated above an AC square wave at 0.25 Hz with a 50% duty cycle was delivered, in all subjects with a current of 0.6 mA, although the device used is capable of delivering more.

Figure 5A:
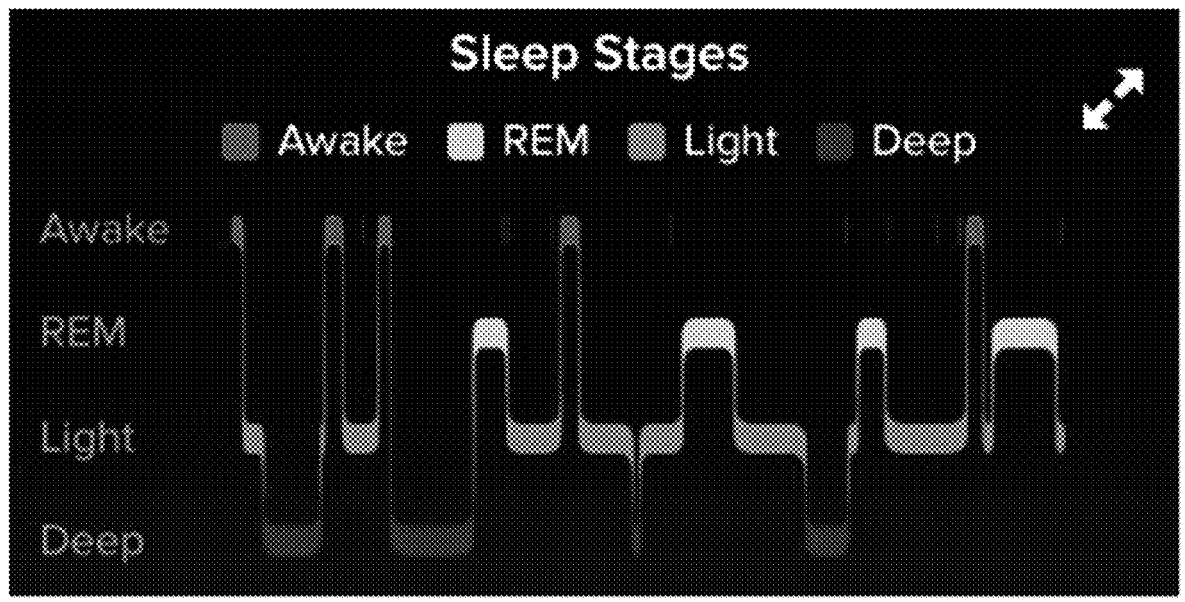
FIG. 5A is a graphical illustration of sleep data from a subject prior to use of the VeNS device, according to one embodiment of the invention.
Figure 5B:
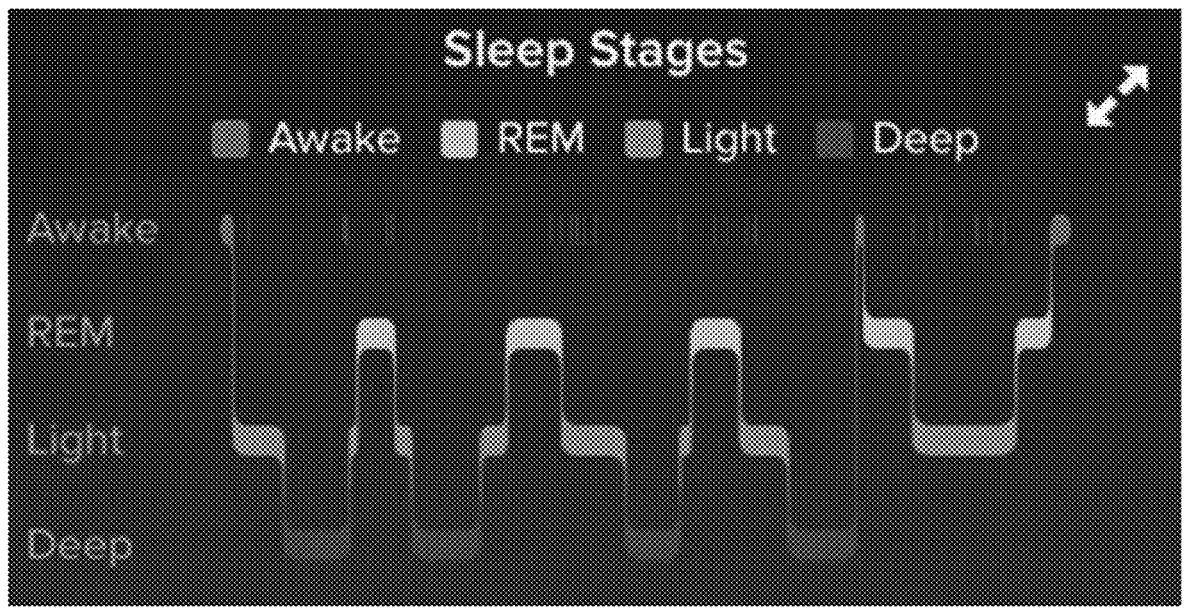
FIG. 5B is a graphical illustration of sleep data from the subject after use of the VeNS device, according to one embodiment of the invention.

FIG. 5A is a graphical illustration of sleep data from a subject prior to use of the VeNS device, illustrating the frequency and duration of sleep stages during sleep. FIG. 5B is a graphical illustration of sleep data from the subject after use of the VeNS device, illustrating the frequency and duration of sleep stages during sleep. The graphical illustrations demonstrate that the amount and duration of REM, Light and Deep sleep stages increased after use of the VeNS device, while the amount and duration of Awake stages decreased.

Figure 6A:
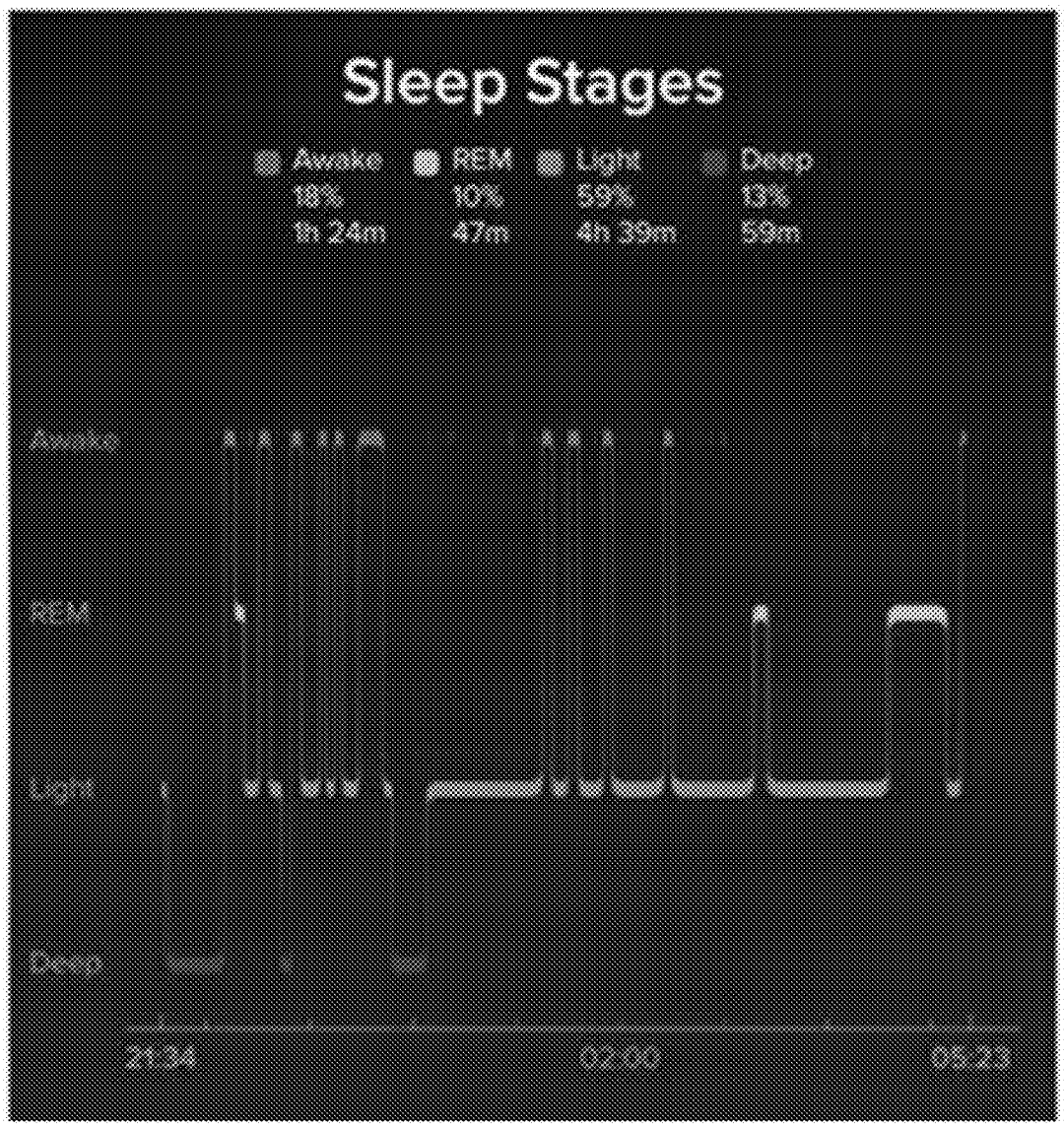
FIG. 6A is a graphical illustration of sleep stages for a subject prior to use of the VeNS device, according to one embodiment of the invention.
Figure 6B:
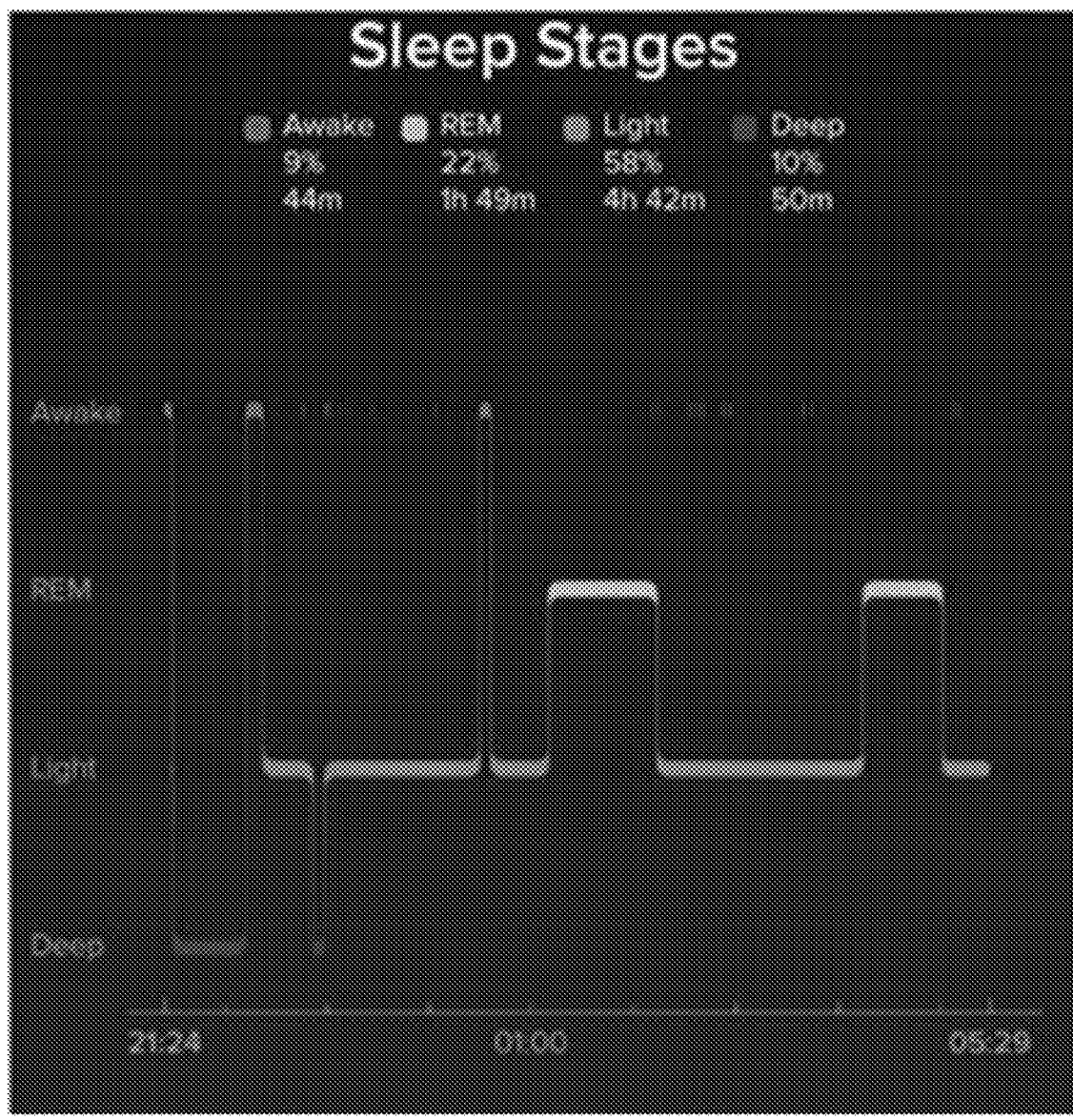
FIG. 6B is a graphical illustration of sleep stages for a subject after use of the VeNS device, according to one embodiment of the invention.

Similarly, FIG. 6A is a graphical illustration of sleep stages for a subject prior to use of the VeNS device, while FIG. 6B is a graphical illustration of sleep stages for a subject after use of the VeNS device. Again, the amount and duration of REM, Light and Deep Sleep Stages increased after use of the device, while the amount and duration of the Awake Sleep Stage significantly decreased.

In another study, a group of participants were measured over a period of 28 days-14 days of pre-treatment measurement to establish a baseline Insomnia Severity Index (ISI) score, and 14 days during treatment to determine the possible effects of the treatment on the average ISI for the subjects. The primary aim of this study was to assess the effect that VeNS had on ISI scores when delivered prior to sleep onset. A secondary aim was to provide initial data indicating 'length of time to effect' that will allow more appropriate design of an RCT. In this study, approximately 30 minutes of VeNS was delivered approximately 1 hour prior to sleep onset using the aforementioned VeNS device from Neurovalens Ltd.

Figure 7:
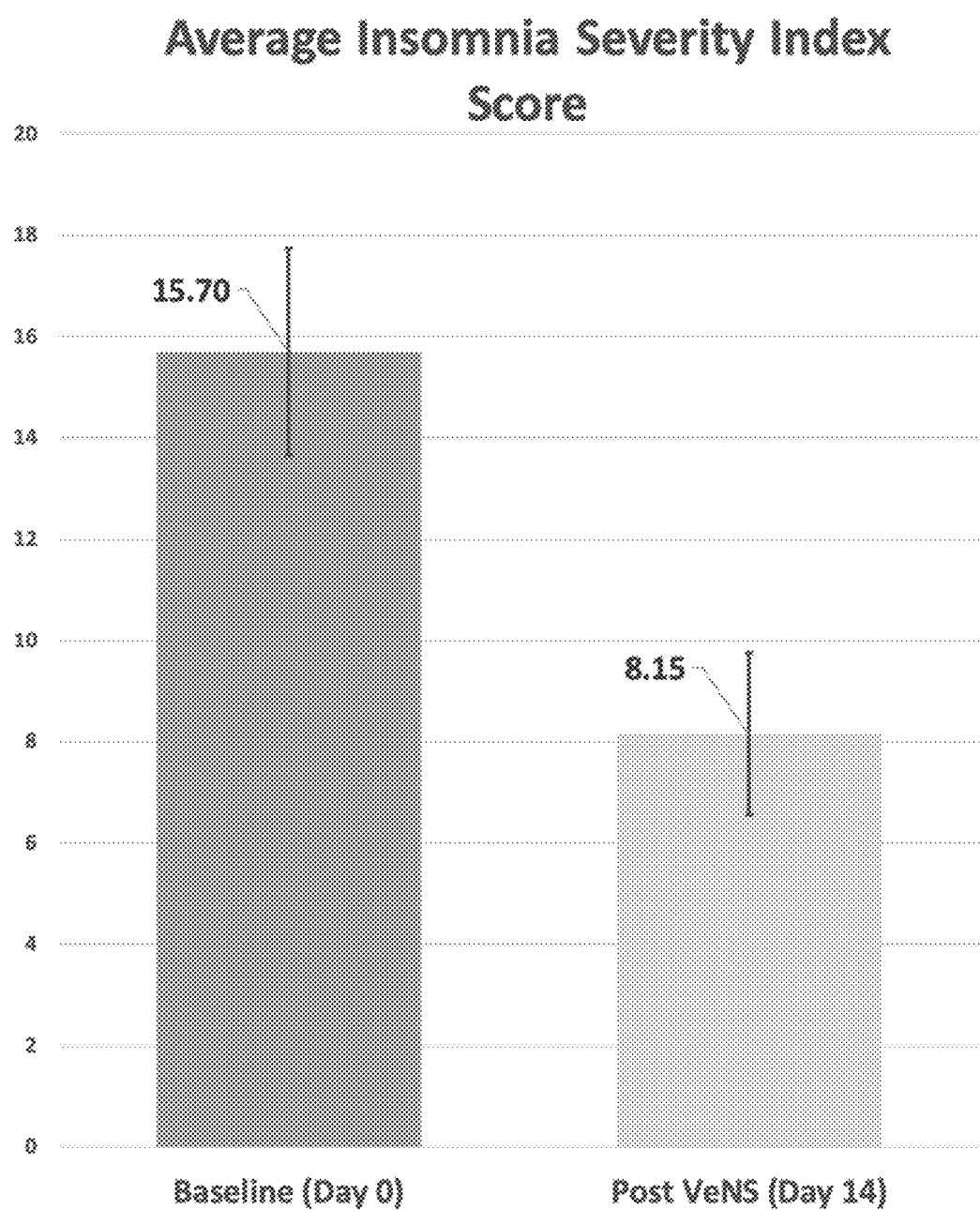
FIG. 7 is a graph illustrating mean Insomnia Severity Index (ISI) scores for a group of subjects before and after delivering VeNS therapy over a period of time, according to one embodiment of the invention.

FIG. 7 is a graph illustrating mean Insomnia Severity Index (ISI) scores for a group of subjects before and after delivering VeNS therapy over a period of time. Mean baseline ISI was calculated as 15.7 (SD 4.7) (moderate insomnia). Repeat ISI score, after 14 days of VeNS sessions, was calculated at 8.15 (SD 3.6) (sub-clinical insomnia). This result was statistically significant ($p<0.00001$).

Figure 8:
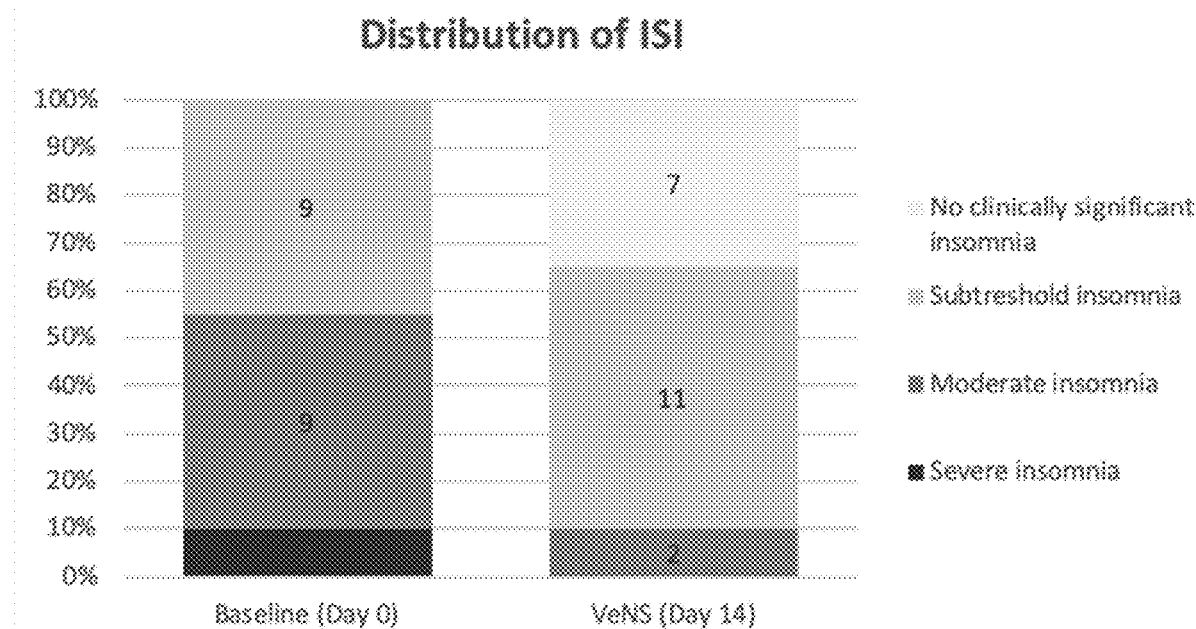
FIG. 8 is a chart displaying a distribution of ISI categories for the group of subjects before and after delivering VeNS therapy over a period of time, according to one embodiment of the invention.

FIG. 8 is a chart displaying a distribution of ISI categories for the group of subjects before and after delivering VeNS therapy over a period of time, illustrating the amount of potential change in clinically-significant levels of insomnia over the measured time period.

Figure 9:
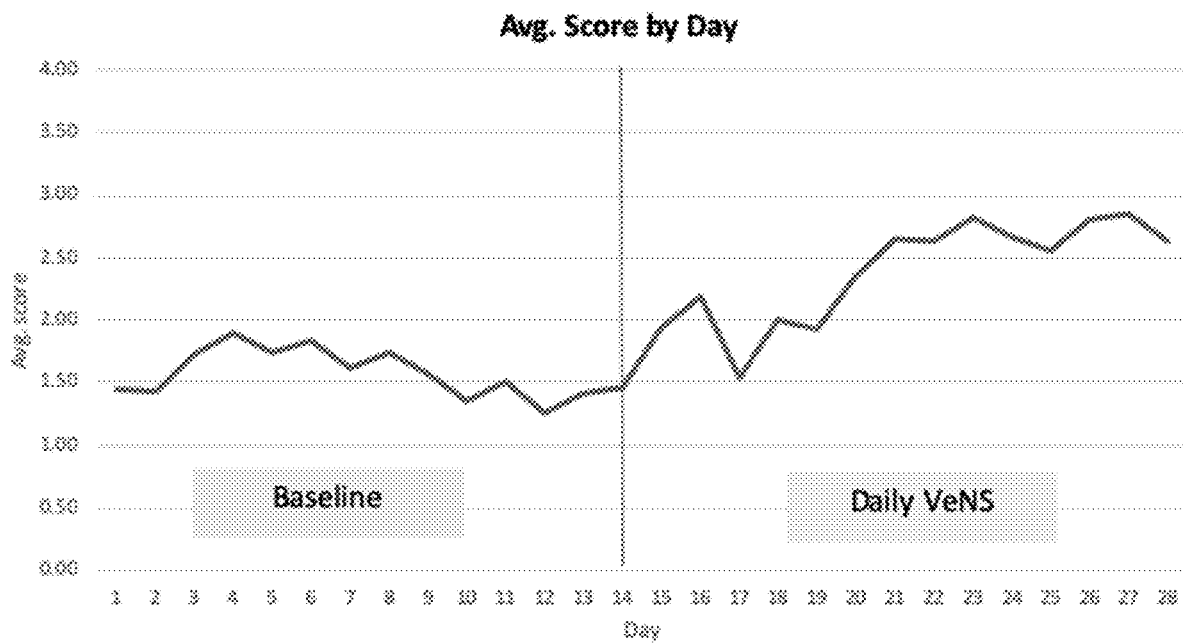
FIG. 9 is a graph displaying the mean subjective score of restfulness of the group of subjects prior to post treatment over time, according to one embodiment of the invention.

FIG. 9 is a graph displaying the mean subjective score by day of restfulness of the group of subjects prior to and post treatment over time (28 days total study period). Self-reported feeling of next day 'restfulness' (Range 0-4) was calculated at 1.6 (SD 0.63) for the baseline period that was established over the first 14 days of the study. With daily VeNS treatment, the mean restfulness score increased to 2.01 (SD 0.79) during week 1 (days 15-21) and 2.67 (SD 0.56) during week 2 (days 22-28).

This pilot study supports the hypothesis that VeNS has a positive impact on ISI scores when delivered on a regular basis prior to sleep onset. Although a subjective measurement, the feeling of 'next day restfulness' appeared to improve significantly within the two week VeNS period. The results indicate that VeNS may have a positive influence on sleep even when delivered prior to sleep onset. Therefore, the mechanism of action for VeNS is more complex than that of a non-specific rocking motion and may be secondary to the direct influence that the vestibular system has on the circadian pacemaker and other sleep-regulating nuclei in the brainstem.

Given the low-risk and non-invasive nature, VeNS may hold potential as a non-pharmaceutical therapy in the management of mild to moderate insomnia.

Vestibular Stimulation Devices

Figure 10:
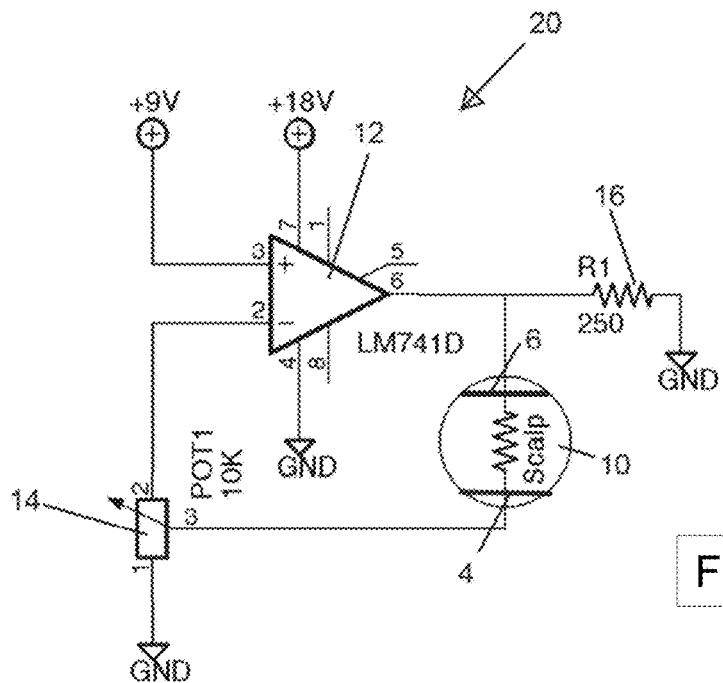
FIG. 10 is a schematic diagram of an exemplary stimulator circuit for a vestibular nerve stimulation (VeNS) device, according to one embodiment of the invention.
Figure 11:
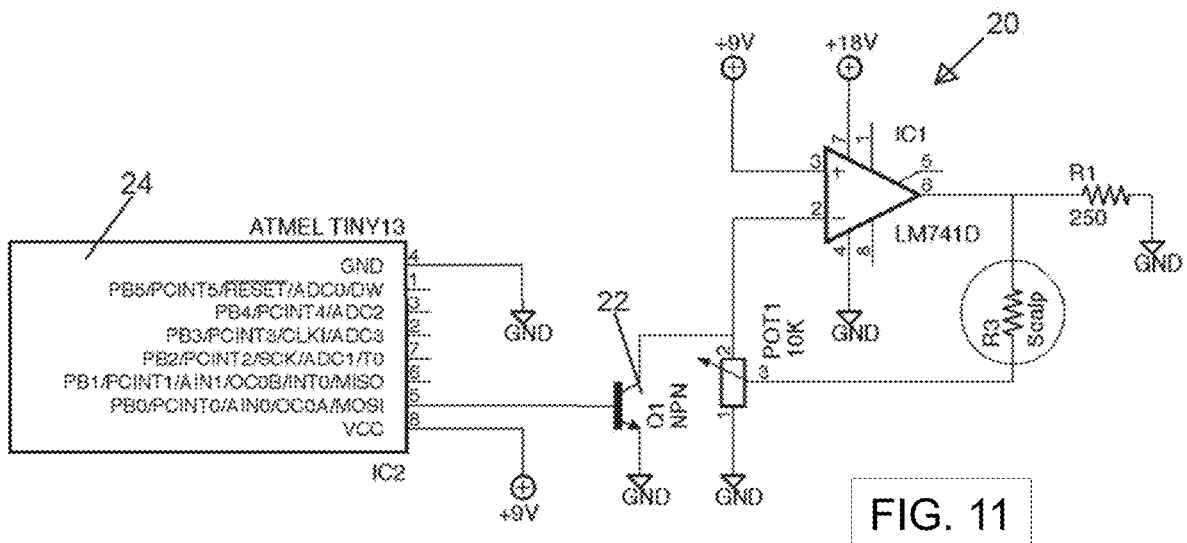
FIG. 11 is a schematic diagram of an alternative embodiment of the stimulator circuit with a gain control component, according to one embodiment of the invention.

FIG. 10 and FIG. 11 illustrate one possible embodiment of the VeNS circuitry that can be employed to carry out the method of the present invention. The device 20 includes a source of time-varying galvanic current that may be software programmable using a microcontroller. In one embodiment, vestibular stimulation may be provided via a head-mounted portable electronic device which is comfortably positioned onto a user's head in an area where stimulation can be delivered to one or both sides of the user's vestibular nerves FIG. 10 illustrates the basic components of an embodiment of the stimulation device 20, which includes an operational-amplifier ("op-amp") based constant-current source. A voltage is placed across the scalp 10 through electrodes 4 and 6 and measured by the op-amp 12. In the exemplary embodiment, op-amp 12 may be a general purpose operational amplifier, an example of which is the LM741 series op-amp, which is widely commercially available. Selection of an appropriate operational amplifier will be within the level of skill in the art. If the voltage returning from the scalp 10 to pin 2 (inverting input) of op-amp 12 is different than the reference voltage +9V at pin 3 (non-inverting input), the operational amplifier draws from the +18V input through pin 7 to increase the amount of voltage output at pin 6, thereby increasing the current across the scalp 10 to maintain a constant current level. Load resistor 16 is 250 ohms. Adjustment of potentiometer 14 provides gain control by decreasing the voltage input into op-amp 12 at pin 2, thus controlling the amount of current flowing across the scalp. In the preferred embodiment, the +9V and +18V inputs are provided by one or more batteries (not shown), or a conventional DC converter may be used with appropriate safety provisions.

The schematic in FIG. 11 adds control components to the basic stimulator circuit 20 of FIG. 1. Transistor 22, powered by the pulse-width-modulation (PWM) output (MOSI (master output/slave input, pin 5) of an ATtiny13 microcontroller 24 (Atmel Corporation, San Jose, CA) or similar device, may be used to control the gain of the stimulator. The PWM causes the transistor to draw more or less of the voltage entering the Op-Amp 12 (pin 2) to ground, thus modulating the amount of current flowing across the scalp.

In a preferred embodiment, the device components and any external interfaces will be enclosed within a housing 30 (shown in FIG. 14) with appropriate user controls 32 for selecting stimulation parameters as appropriate. Note that a knob is shown for illustrative purposes only and that other types of controls, including switches, buttons, pressure bumps, slides, touch screens or other interface devices may be used. Optional design components that may be added to expand the functionality of the device include a memory storage device, such as a memory card or electrically erasable programmable read-only memory (EEPROM), which will allow the time, duration, and intensity of stimulations to be recorded. This can be accomplished by programming the microcontroller 24 to output a logic-level 3.4V pulse (TTL (transistor-transistor logic)) from the remaining digital out (MISO (master input/slave output, pin 6) to a secure digital (SD) memory card, EEPROM, USB flash drive or other data storage device via an appropriate port on the device housing. Additionally, the +18V input may be derived by integrating a charge pump, or DC-DC step-up converter, such as the MAX629 or MAX1683 (not shown). This design feature would have the benefit of reducing the size of the device by producing the necessary +18V input from smaller batteries, which can be disposable or lithium ion rechargeable. Additional features may include wireless communication circuitry, as is known in the art, for programming and/or data collection from a remote computing device, which may include a personal computer, smart phone or tablet computer.

Other functions for implementing VeNS in the present invention may include the ability to pulse the current at precise intervals and durations, in a sinusoidal wave with adjustable amplitude and period, and even switch polarity at precise intervals.

Additional options for facilitating and/or enhancing the administration of VeNS may include a built-in biofeedback capability to adjust the stimulation parameters for optimal effect based on signals generated by sensors that monitor the subject's activity and/or biometric characteristics, such as motion, position, heart rate, etc. For example, real-time heart measured by a heart-rate sensor or monitor can be used as input into the VeNS device, triggering an automatic adjustment of the sinusoidal VeNS frequency to an appropriate, possibly pre-programmed, fraction of the cardiac frequency. Real-time data on the user's motion or position measured by accelerometers may also be used as input to control stimulation, to improve effectiveness and safety. For example, treatment could be terminated if excessive motion or change in the user's position is detected, or the user can be alerted about changes in position that could have adverse effects. The heart rate sensor/monitor and/or accelerometers may be separate devices that communicate with the inventive VeNS device through a wired or wireless connection. Alternatively, sensors may be incorporated directly into the VeNS device to form a wearable "sense-and-treat" system. As new sensors are developed and adapted to mobile computing technologies for "smart", wearable mobile health devices, a "sense-and-treat" VeNS device may provide closely tailored stimulation based on a wide array of sensor data input into the device.

Figure 12:
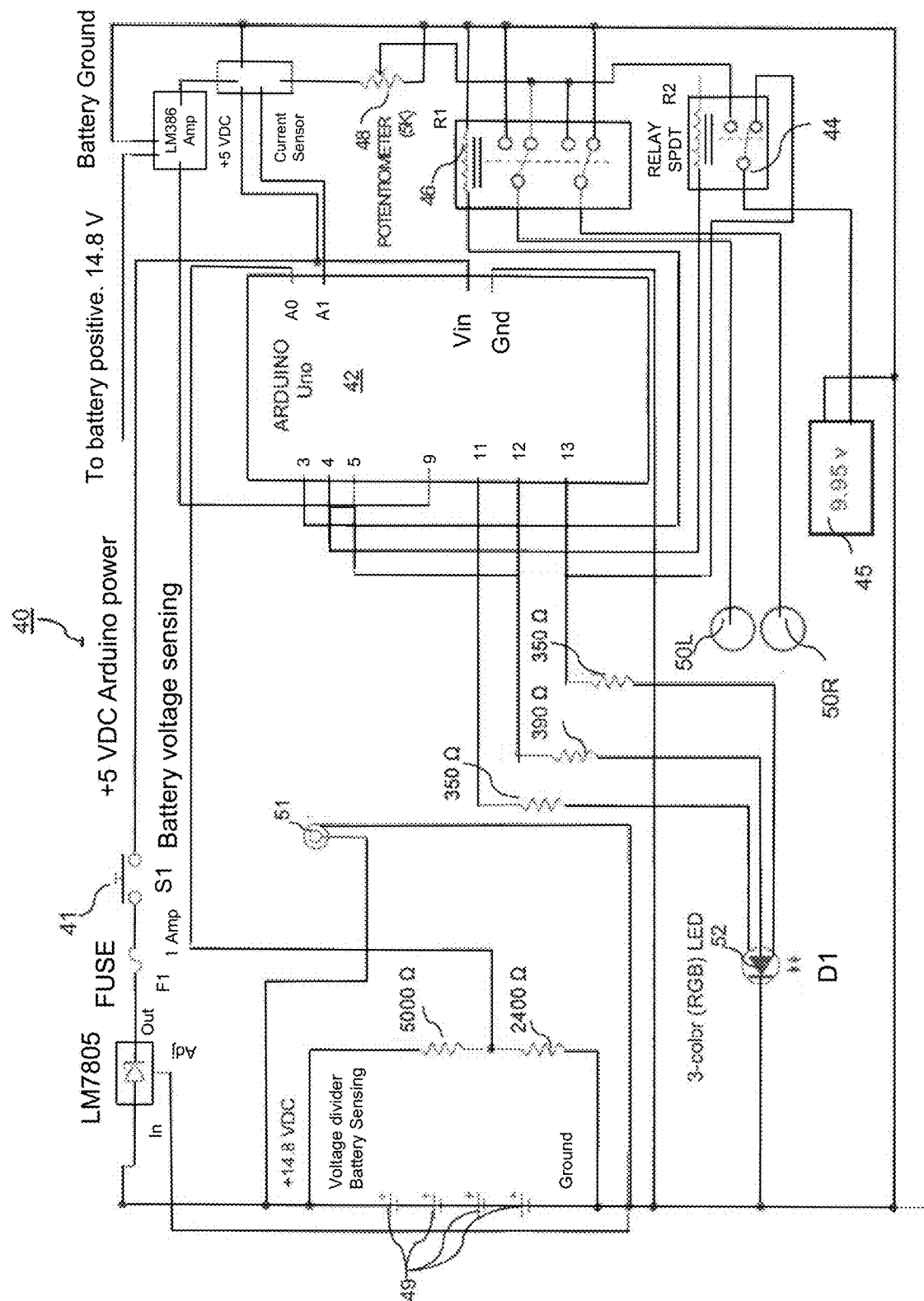
FIG. 12 is a schematic diagram of a second alternative embodiment of the stimulator device, according to one embodiment of the invention.

FIG. 12 schematically illustrates an exemplary prototype of the inventive device 40 implemented using the widely commercially-available ARDUINO® Uno single board microcontroller 42 (Arduino, LLC, Cambridge, MA), which is based on the ATmega328 microcontroller (ATMEL® Corporation, San Jose, CA). Microcontroller 42 includes fourteen digital input/output pins (of which six can be used as pulse width modulation (PWM) outputs), six analog inputs, a 16 MHz ceramic resonator, a USB connection, a power jack, an ICSP header, and a reset button. The +14.8 V DC power to the circuit is provided by batteries 49. For example, four lithium ion batteries, each providing 3.7V (1300 mAh) are used, and are preferably rechargeable via charging port 51.

Figure 13A:
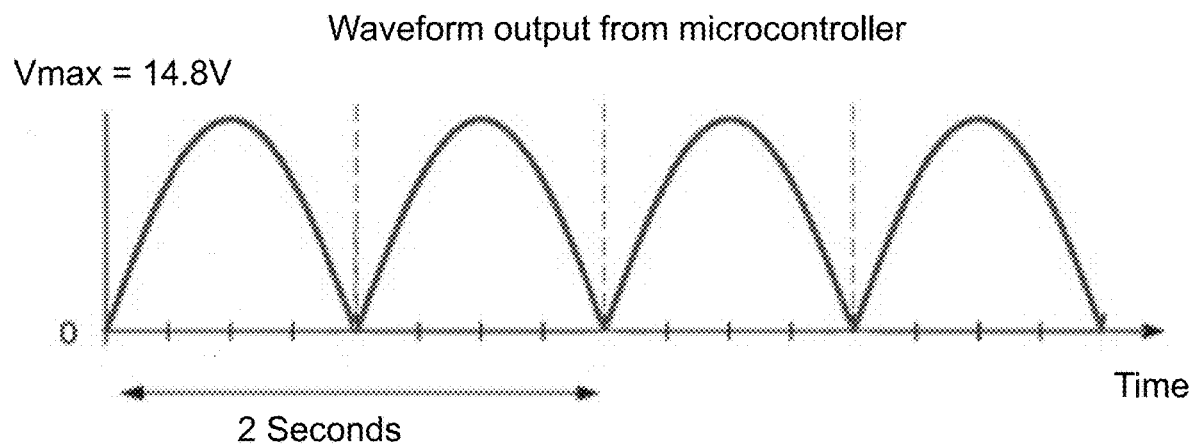
FIGS. 13A and 13B illustrate exemplary wave forms generated by the device, according to one embodiment of the invention.

The PWM allows the output waveform to be accurately controlled. In this case, the waveform takes a repeating half-sine wave pattern in a positive deflection, as shown in FIG. 13A. The frequency has been predefined as 0.25 Hz, but may be set to a different value by manual control or in response to input from a sensor, such as a heart rate sensor (see, e.g., FIG. 14). The user can manually control the amplitude by adjusting the potentiometer 48, allowing a range of 0 to 14.8V to be supplied to the electrodes. This adjustment may be effected by rotating a knob, moving a slide (physically or via a touch screen), or any other known user control mechanism. Alternatively, the potentiometer setting can automatically adjust in response to an input signal from a sensor. Relay 44 communicates the voltage adjustment to a graphical display 45 to provide a read-out of the selected voltage and/or current.

Figure 13B:
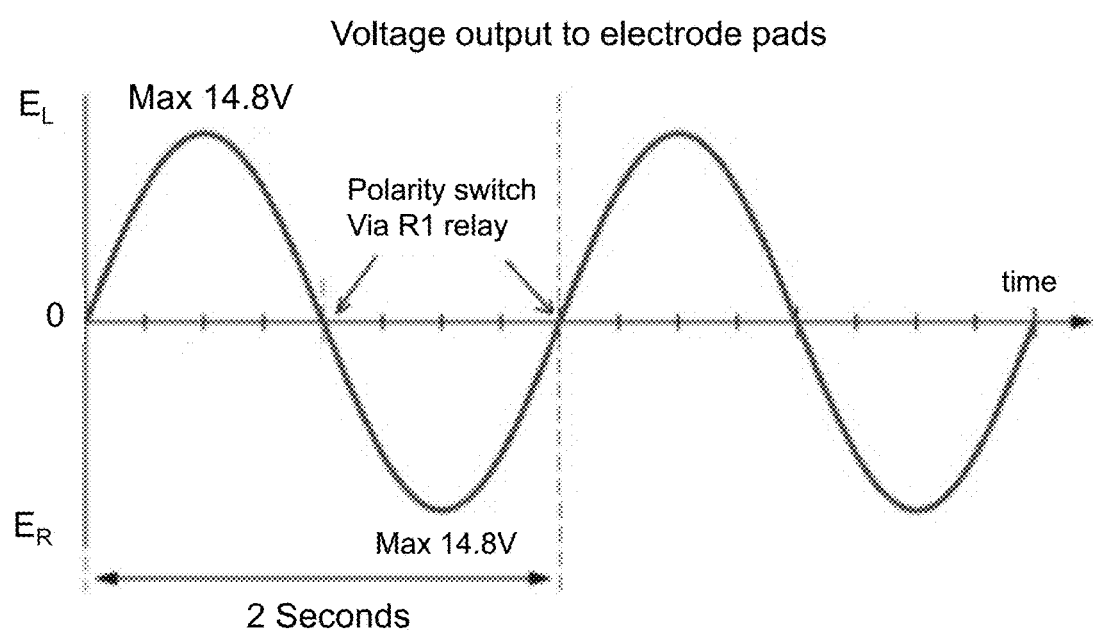

A relay 46 may be employed to effectively reverse the polarity of the current with every second pulse. The effect of this is shown in FIG. 13B, where the sinusoidal pattern changes polarity, thus generating a complete sine waveform to produce alternating periods of stimulation, on the order of 1 second in duration, to the left and right mastoid electrodes 50L and 50R.

The device may optionally include a three color LED 52 that provides a visual display of device conditions, i.e., diagnostic guidance, such as an indication that the device is working correctly or that the battery requires recharging.

Optional design components may include a touch screen configuration that incorporates the potentiometer controls, a digital display of voltage and current, plus other operational parameters and/or usage history. For example, remaining battery charge, previous stimulation statistics and variations in resistance could be displayed. Additional features may include controls for alterations in the waveform such as change of frequency and change of wave type (for example square, pulse or random noise). The ARDUINO® microprocessor platform (or any similar platform) is ideally suited to incorporate feedback control or manual control of frequency, intensity or other stimulation parameters based on an external signal source. For example, the ARDUINO® microprocessor platform, if provided with BLUETOOTH® capability, can be wirelessly controlled by an iPHONE®, ANDROID®, or other smart phone, laptop or personal computer, tablet or mobile device, so that the touchscreen of the mobile device can be used to control and/or display the VeNS stimulation parameters rather than requiring a dedicated screen on the device. The mobile device may also be configured to store and analyze data from previous stimulations, providing trends and statistics about long periods of stimulation, such as over 6 months. Applications of this could allow for programs to monitor and guide users on their progress and goals, highlighting body measurements and changes in weight relative to the periods of stimulation.

An exemplary operational sequence for the embodiment of FIG. 12 for use in promoting sleep may include the following steps:

When the push button power switch 41 is activated, the battery(ies) 49 supply 5 volts DC to the microprocessor 42 through a 5 volt regulator and a 1 amp fuse (shown in the figure but not separately labeled.)

The LED 52 will flash green three times to indicate the power is "on". If the blue light flashes the battery needs charging. While the voltage is supplied to the electrodes 50L and 50R, the LED 52 will flash red at regular intervals, e.g., 30 seconds to a minute.

The microprocessor 42 generates a 0.75 VDC half wave sign wave. The voltage is amplified to 14.8 volts by the amplifier. The sine wave completes one-half cycle in 1 second (i.e., the frequency of the sine wave is 0.25 Hz). The voltage can be varied by the potentiometer 48 from 0 to 14.8 volts.

After a half cycle is completed, relay 46 switches polarity of the electrodes 50L, 50R and the microprocessor 42 sends another half cycle. The relay 46 again switches polarity and continues for as long as the unit is "on". This sends a full sine wave of up to +14.8 VDC to the electrodes, with the full voltage swing modulated by the potentiometer 48.

A digital display 45 provides a visual indication of the voltage and current delivered to the electrodes 50L, 50R. Depending on the size and complexity of the display, voltage and current values may be displayed simultaneously or alternately for a short duration, e.g., 3 seconds.

Other device options may include user controls to allow the current to be pulsed at precise intervals and durations, a sinusoidal wave to be generated with adjustable amplitude and period, and/or to switch polarity at precise intervals. External control and monitoring via a smart phone or other mobile device as described above may also be included. Further input and processing capability for interfacing and feedback control through external or internal sensors may be included.

FIG. 14 illustrates an exemplary VeNS electrode 34 positioned on the skin behind the pinna of the left ear 36, and over the left mastoid process, of a subject to be treated. The mastoid process is represented by dashed line 38. The right electrode (not shown) would be placed in the same manner on the skin over the right mastoid process and behind the right pinna. It should be noted that the illustrated placement of the electrodes is provided as an example only. In fact, laterality of the electrode application, e.g., electrodes precisely over both mastoid processes, is not believed to be critical, as long as each electrode is in sufficient proximity to the vestibular system to apply the desired stimulation. The electrodes 34 are connected to stimulation device 40 (inside housing 30) by leads 33. Manual control means, illustrated here as a simple knob 32, may be operated to control the current or other parameters. As described above, alternative control means include a slide, touch screen, buttons or other conventional control devices. External control signals, for example, a signal from a heart rate monitor 35, may be input into the device either wirelessly, as illustrated, or by leads running between the sensor and the device. Electrodes such as the widely commercially available 2×2 inch platinum electrodes used for transcutaneous electrical nerve stimulation (TENS) may be used in order to minimize any possible skin irritation. A conducting gel 37 may be applied between the subject's scalp and the contact surface of the electrodes to enhance conduction and reduce the risk of skin irritation.

The amount of current the subject actually receives depends on the scalp resistance ($I_{scalp} = V_{electrodes}/R_{scalp}$), which may vary as the user perspires, if the electrode position changes, or if contact with the skin is partially lost. It appears that the current levels quoted in the literature could only be delivered if the scalp resistance was much lower than it actually is. Measurements conducted in conjunction with the development of the inventive method and device indicate that the trans-mastoid resistance is typically between 200 to 500 k-Ohm. Thus, if a VeNS device were actually being used to deliver 1 mA, the voltage would be between 200 to 500V according to Ohm's law. The battery-powered devices that are usually used to administer VeNS are simply not capable of generating such an output. Hence, the existing reports appear to be inaccurate with regard to the actual current being delivered in VeNS.

Prior art designs lack consideration for each subject's unique scalp resistance, and therefore may not deliver an effective current to each patient. In the present invention, this limitation can be overcome by taking into account inter-subject scalp resistance variability as well as compensating for fluctuations in the scalp resistance that may occur throughout the procedure. To compensate for slight and fluctuating changes in scalp resistance during the administration of current, the inventive VeNS device may include an internal feedback loop that continuously compares the desired current against the actual measured current across the scalp and automatically compensates for any differences. If $R_{scalp}$ increases, the $V_{electrodes}$ increases to compensate. Conversely, voltage decreases when $R_{scalp}$ drops. This dynamic feedback compensation loop provides constant current across the scalp for the duration of the procedure regardless of fluctuating changes in electrode-scalp impedance.

Computer-Enabled Embodiment

Figure 15:
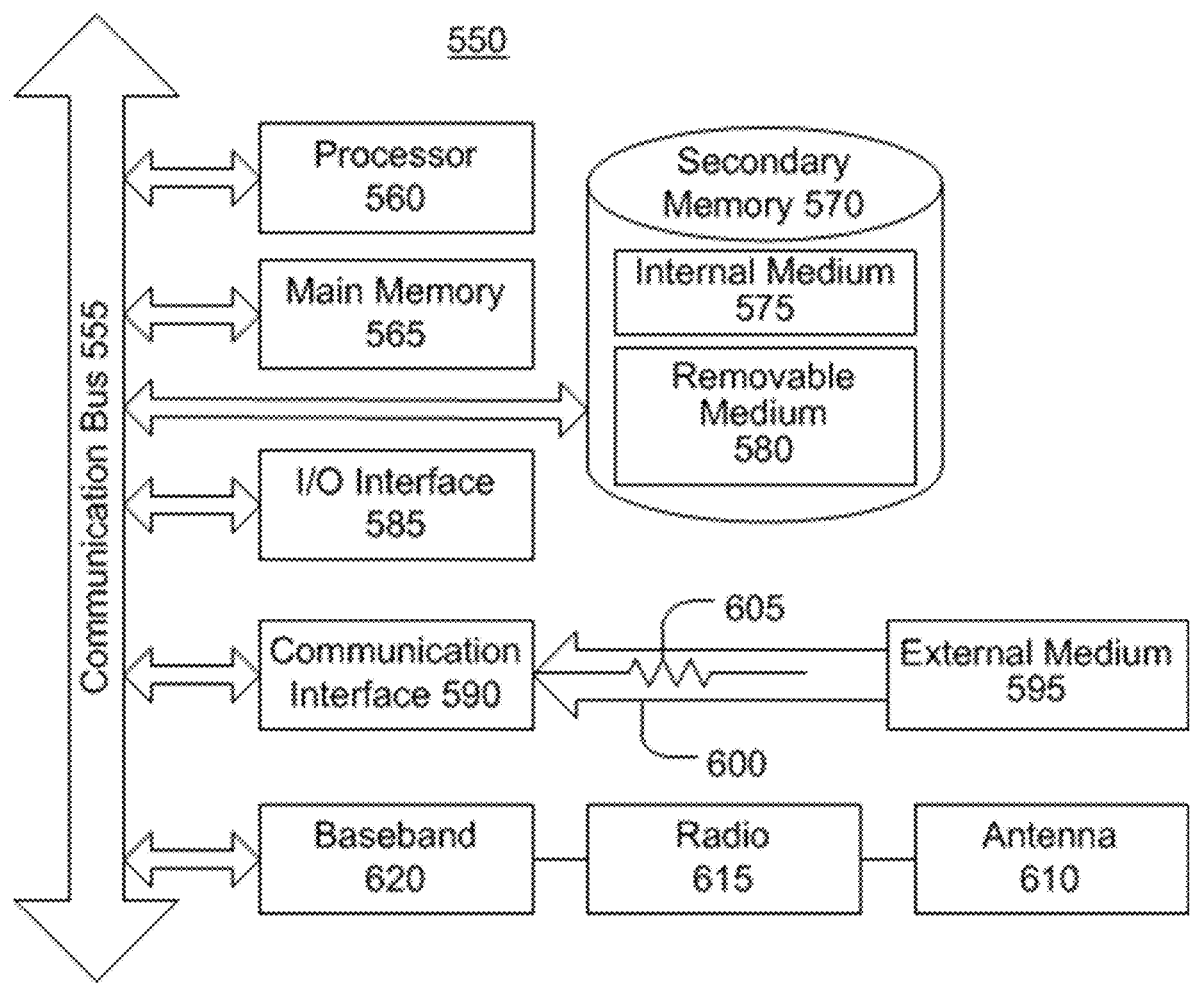
FIG. 15 is a block diagram illustrating an example wired or wireless processor enabled device that may be used in connection with various embodiments described herein.

FIG. 15 is a block diagram illustrating an example wired or wireless system 550 that may be used in connection with various embodiments described herein. For example the system 550 may be used as or in conjunction with a vestibular nerve stimulation device as previously described with respect to FIGS. 1-6. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method of promoting sleep in a human subject through delivery of vestibular nerve stimulation (VeNS), the method comprising:
    daily, prior to a desired sleep time of the human subject, positioning at least one electrode into electrical contact with the human subject and proximate to a location of a vestibular system of the human subject;
    delivering VeNS to the human subject from a current source connected with the at least one electrode, wherein the VeNS comprises a subsensory frequency that avoids creating a rocking sensation in the human subject and is delivered for a treatment session of approximately 30 minutes to approximately 60 minutes; and after the treatment session, removing the at least one electrode from the human subject.

2. The method of claim 1, wherein the steps of positioning and delivering are initiated within approximately 4 hours of the desired sleep time of the human subject.

3. The method of claim 1, wherein the steps of positioning and delivering are initiated within approximately 1 hour of the desired sleep time of the human subject.

4. The method of claim 1, further comprising delivering the VeNS using an alternating current (AC) square wave.

5. The method of claim 4, further comprising delivering the VeNS using an AC square wave at a frequency below 0.5 Hz with an approximately 50 percent duty cycle.

6. The method of claim 1, further comprising delivering the VeNS via a bipolar binaural application.

7. The method of claim 1, wherein delivering VeNS comprises delivering an alternating polarity square wave having a frequency of approximately 0.25 Hz, a current range of approximately 0.01-1 mA, and an approximately 50 percent duty cycle.

8. The method of claim 1, further comprising:
during delivering of VeNS, monitoring one or more of activity and biometric characteristics of the human subject and terminating the treatment session based upon detection of a pre-determined amount of motion or a change in position of the human subject.

9. A method of treating insomnia in a subject with vestibular nerve stimulation, comprising:
daily, prior to a desired sleep time of the subject, positioning at least one electrode into electrical contact with the subject and proximate to a location of a vestibular system of the subject; and delivering VeNS to the subject from a current source connected with the at least one electrode, wherein the VeNS comprises a subsensory frequency that avoids creating a rocking sensation in the subject and is delivered for a treatment period of approximately 30 minutes to approximately 60 minutes prior to the subject's desired sleep time; and after the treatment period ends, removing the at least one electrode from the subject.

10. The method of claim 9, wherein the steps of positioning and delivering are initiated within approximately 4 hours of the desired sleep time of the subject.

11. The method of claim 9, wherein the steps of positioning and delivering are initiated within approximately 1 hour of the desired sleep time of the subject.

12. The method of claim 9, further comprising delivering the VeNS using an alternating current (AC) square wave.

13. The method of claim 12, further comprising delivering the VeNS using an AC square wave at a frequency below 0.5 Hz with an approximately 50 percent duty cycle.

14. The method of claim 9, further comprising delivering the VeNS via a bipolar binaural application.

15. The method of claim 9, wherein delivering VeNS comprises delivering an alternating polarity square wave having a frequency of approximately 0.25 Hz, a current range of approximately 0.01-1 mA, and an approximately 50 percent duty cycle.

16. The method of claim 9, further comprising:
during delivering of VeNS, monitoring one or more of activity and biometric characteristics of the subject and terminating the treatment period based upon detection of a pre-determined amount of motion or a change in position of the subject.

* * * * *